United States Patent [19]

Coates et al.

[11] Patent Number: 5,008,272
[45] Date of Patent: Apr. 16, 1991

[54] LACTAM DERIVATIVES

[75] Inventors: Ian H. Coates, Hertford; Alexander W. Oxford; Peter C. North, both of Royston, all of England

[73] Assignee: Glaxo Group Limited, England

[21] Appl. No.: 393,145

[22] Filed: Aug. 14, 1989

[30] Foreign Application Priority Data

Aug. 15, 1988 [GB] United Kingdom ............. 8819382
Sep. 1, 1988 [GB] United Kingdom ............. 8820647

[51] Int. Cl.$^5$ .................. A61K 31/445; C07D 471/04
[52] U.S. Cl. ......................................... 514/292; 546/86
[58] Field of Search ......................... 514/292; 546/86

[56] References Cited

U.S. PATENT DOCUMENTS

| 4,636,563 | 1/1987 | Abou-Gharbia | 546/87 |
|---|---|---|---|
| 4,695,578 | 9/1987 | Coates | 514/397 |
| 4,725,615 | 2/1988 | Coates | 514/397 |
| 4,739,072 | 4/1988 | Oxford | 548/336 |
| 4,749,718 | 6/1988 | Coates | 514/397 |
| 4,754,038 | 6/1988 | Abou-Gharbia | 546/87 |
| 4,798,896 | 1/1989 | Abou-Gharbia | 546/87 |
| 4,808,581 | 2/1989 | Oxford | 514/212 |
| 4,814,344 | 3/1989 | Humber et al. | 514/397 |
| 4,822,881 | 4/1989 | Coates | 540/603 |
| 4,859,662 | 8/1989 | Coates et al. | 514/212 |

FOREIGN PATENT DOCUMENTS

| 0238411 | 9/1987 | European Pat. Off. |
| 0306323 | 3/1989 | European Pat. Off. |
| 0392663 | 10/1990 | European Pat. Off. |

Primary Examiner—Mary C. Lee
Assistant Examiner—Jacqueline Haley
Attorney, Agent, or Firm—Bacon & Thomas

[57] ABSTRACT

The invention provides potent and selective antagonists of 5-HT and 5-HT$_3$ receptors which are tricyclic lactams of the general formula (I)

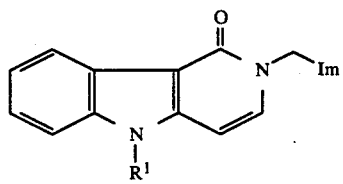

wherein
Im represents an imidazolyl group of the formula:

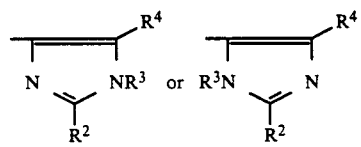

and R$^1$ represents a hydrogen atom or a group selected from C$_{1-6}$alkyl, C$_{3-6}$alkenyl, C$_{3-10}$alkynyl, C$_{3-7}$cycloalkyl, C$_{3-7}$cycloalkylC$_{1-4}$alkyl, phenyl, phenylC$_{1-3}$alkyl, phenylmethoxymethyl, phenoxyethyl, phenoxymethyl, —CO$_2$R$^5$, —COR$^5$, —CONR$^5$R$^6$ or —SO$_2$R$^5$;
one of the group represented by R$^2$, R$^3$ and R$^4$ is a hydrogen atom or a C$_{1-6}$ alkyl, C$_{3-7}$cycloalkyl, C$_{3-6}$alkenyl, phenyl or phenylC$_{1-3}$alkyl group, and each of the other two groups, which may be the same or different, represents a hydrogen atom or a C$_{1-6}$alkyl group;
and physiologically acceptable salts and solvates thereof.

7 Claims, No Drawings

LACTAM DERIVATIVES

This invention relates to lactam derivatives, to processes for their preparation, to pharmaceutical compositions containing them and to their medical use.

In particular the invention relates to compounds which are potent and selective antagonists of 5-hydroxytryptamine (6-HT) at 5-HT receptors of the type located on terminals of primary afferent nerves. Receptors of this type are now designated as 5-HT$_3$ receptors and are also present in the central nervous system. 5-HT occurs widely in the neuronal pathways in the central nervous system and disturbance of these 5-HT containing pathways is known to alter behavioural syndromes such as mood, psychomotor activity, appetite and memory.

Compounds having antagonist activity at 5-HT$_3$ receptors have been described previously.

Thus for example German Offenlegungsschrift No. 3740352 discloses compounds which may be represented by the general formula:

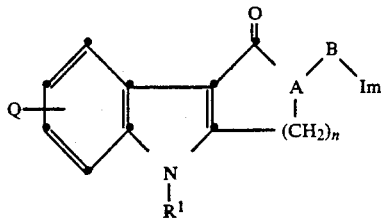

wherein
Im represents an imidazolyl group of the formula:

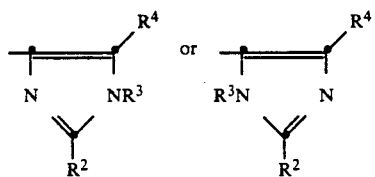

$R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl-, phenyl, phenyl$C_{1-3}$alkyl-, —CO$_2$R$^5$, —CONR$^5$R$^6$ or —SO$_2$R$^5$ (wherein R$^5$ and R$^6$, which may be the same or different, each represents a hydrogen atom, a $C_{1-6}$alkyl or $C_{3-7}$-cycloalkyl group, or a phenyl or phenyl$C_{1-4}$alkyl- group, in which the phenyl group is optionally substituted by one or more $C_{1-4}$alkyl, $C_{1-4}$alkoxy or hydroxy groups or halogen atoms, with the proviso that R$^5$ does not represent a hydrogen atom when R$^1$ represents a group —CO$_2$R$^5$ or —SO$_2$R$^5$);

one of the groups represented by R$^2$, R$^3$ and R$^4$ is a hydrogen atom or a, $C_{1-6}$alkyl, $C_{3-7}$cycloalkyl, $C_{3-6}$alkenyl, phenyl or phenylic $C_{1-3}$alkyl- group, and each of the other two groups, which may be the same or different, represents a hydrogen atom or a $C_{1-6}$alkyl group; Q represents a hydrogen or a halogen atom, or a hydroxy, $C_{1-4}$alkoxy, phenyl$C_{1-3}$alkoxy- or $C_{1-6}$alkyl group or a group —NR$^7$R$^8$ or —CONR$^7$R$^8$ (wherein R$^7$ and R$^8$, which may be the same or different, each represents a hydrogen atom or a $C_{1-4}$alkyl or $C_{3-4}$alkenyl group, or together with the nitrogen atom to which they are attached form a saturated 5 to 7 membered ring);

n represents 1, 2 or 3;
and A—B represents the group CH—CH$_2$ or C=CH; and physiologically acceptable salts and solvates thereof.

We have now found a novel group of compounds which differ in structure from those described previously, and which are potent antagonists of the effect of 5-HT at 5-HT$_3$ receptors.

The present invention provides a tricyclic lactam of the general formula (I):

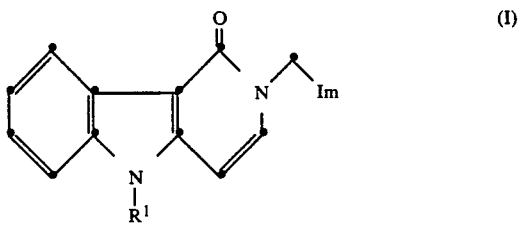

wherein
Im represents an imidazolyl group of the formula:

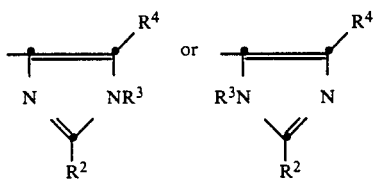

and R$^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl $C_{1-4}$alkyl, phenyl, phenyl$C_{1-3}$alkyl, phenylmethoxymethyl, phenoxyethyl, phenoxymethyl, —CO$_2$R$^5$, —COR$^5$, —CONR$^5$R$^6$ or —SO$_2$R$^5$ (wherein R$^5$ and R$^6$, which may be the same or different, each represents a hydrogen atom, a $C_{1-6}$alkyl or $C_{3-7}$cycloalkyl group, or a phenyl or phenyl$C_{1-4}$alkyl group, in which the phenyl group is optionally substituted by one or more $C_{1-4}$ alkyl, $C_{1-4}$alkoxy or hydroxy groups or halogen atoms, with the proviso that R$^5$ does not represent a hydrogen atom when R$^1$ represents a group —CO$_2$R$^5$ or —SO$_2$R$^5$);

one of the groups represents by R$^2$, R$^3$ and R$^4$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group; and physiologically acceptable salts and solvates thereof.

Suitable physiologically acceptable salts of the compounds of general formula (I) include acid addition salts formed with organic or inorganic acids for example, hydrochlorides, hydrobromides, sulphates, alkyl- or arylsulphonates (e.g. methanesulphonates or p-toluenesulphonates), phosphates, acetates, citrates, succinates, tartrates, fumarates and maleates. The solvents may, for example, be hydrates.

All optical isomers of compounds of general formula (I) and their mixtures including the racemic mixtures thereof, and all the geometric isomers of compounds of formula (I), are embraced by the invention.

Referring to the general formula (I), an alkyl group may be a straight chain or branched chain alkyl group, for example, methyl, ethyl, propyl, prop-2-yl, butyl, but-2-yl, 2-methylprop-2-yl, 2-methylprop-2-yl, pentyl, pent-3-yl or hexyl. A $C_{3-6}$alkenyl group may be, for example, a propenyl or butenyl group. A $C_{3-10}$alkynyl group may be, for example, a prop-2-ynyl group. When $R^1$ represents a $C_{3-6}$alkenyl or $C_{3-10}$alkynyl group, or $R^3$ represents a $C_{3-6}$alkenyl group, the double or triple bond may not be adjacent to the nitrogen atom. A phenyl$C_{1-3}$alkyl group may be, for example, a benzyl, phenethyl or 3-phenylpropyl group. A $C_{3-7}$cycloalkyl group may be, for example, a cyclopropyl, cyclobutyl, cyclopentyl, cyclohexyl or cycloheptyl group.

A preferred class of compounds of formula (I) is that wherein $R^1$ represents a hydrogen atom or, more preferably, a $C_{1-3}$alkyl (e.g. methyl) group.

Another preferred class of compounds of formula (I) is that in which $R^2$, $R^3$ and $R^4$ each independently represent a hydrogen atom or a $C_{1-4}$alkyl (e.g. methyl) group. A further preferred class of compounds is that wherein $R^2$ and $R^3$ each represent a hydrogen atom, and $R^4$ is a $C_{1-3}$alkyl (e.g. methyl) group.

A particularly preferred compound according to the invention is: 2,5-dihydro-5-methyl-2-[(5-methyl-1$\underline{H}$-imidazol-4-yl)methyl]-1$\underline{H}$-pyrido[4,3-b]indol-1-one and its physiologically acceptable salts and solvates.

The potent and selective antagonism of 5-HT at 5-HT$_3$ receptors by the compounds of the invention may be demonstrated by their ability to inhibit 3-(5-methyl-1$\underline{H}$-imidazol-4-yl)-1-[1-(methyl-t$_3$)-1$\underline{H}$-indol-3yl]-1-propanone binding n rat entorhinal cortex homogenates (following the general procedure described by G. Kilpatrick et al. in Nature, 1987, 330, 746), and /or by their ability to inhibit the 5-HT-induced depolarisation of the rat isolated vagus nerve preparation.

Compounds of formula (I), which antagonise the effect of 5-HT at 5-HT$_3$ receptors, are useful in the treatment of conditions such as psychotic disorders (e.g. schizophrenia and mania); anxiety; and nausea and vomiting, particularly that associated with cancer chemotherapy and radiotherapy. Compounds of formula (I) are also useful in the treatment of gastric stasis; symptoms of gastrointestinal dysfunction such as occur with dyspepsia, peptic ulcer, reflux oesophagitis, flatulence and irritable bowel syndrome; migraine, obesity and conditions such as bulimia; and pain. Compounds of formula (I) may also be used in the treatment of dependency on drugs and substances of abuse, depression, and dementia and other cognitive disorders.

According to another aspect, the invention provides a method of treatment of a human or animal subject suffering from a psychotic disorder such as schizophrenia or mania; or from anxiety; nausea or vomiting; gastric stasis; symptoms of gastrointestinal dysfunction such as dyspepsia, reflux oesophagitis, peptic ulcer, flatulence and irritable bowel syndrome, migraine; obesity and conditions such as bulimia; pain; dependency on drugs or substances of abuse; depression; or dementia or another cognitive disorder which comprises administering an effective amount of a compound of formula (I) or a physiologically acceptable salt or solvate thereof.

Accordingly, the invention also provides a pharmaceutical composition which comprises at least one compound selected from compounds of the general formula (I), and their physiologically acceptable salts and solvates (e.g. hydrates), for use in human or veterinary medicine, and formulated for administration by any convenient route.

Such compositions may be formulated in conventional manner one or more physiologically acceptable carriers and/or excipients.

Thus the compounds according to the invention may be formulated or oral, buccal, parenteral or rectal administration or in a form suitable for administration by inhalation or insufflation (either through the mouth or nose).

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxylpropyl methylcellulose); fillers (e.g. lactose, microcrystalline cellulose or calcium hydrogen phosphate); lubricants (e.g. magnesium stearate, talc or silica); disintegrants (e.g. potato starch or sodium starch glycollate); or wetting agents (e.g. sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily or aqueous vehicle, and may contain formulatory agents such as suspending, stabilising and/or dispensing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

In addition to the formulations described previously, the compounds of the invention may also be formulated as depot preparations. Such long acting formulations may be administered by implantation (for example subcutaneously or intramuscularly) or by intramuscular injection. Thus, for example, the compounds of the invention may be formulated with suitable polymeric or hydrophobic materials (for example as an emulsion in an acceptable oil) or ion exchange resins, or as sparingly soluble derivatives, for example, as a sparingly soluble salt.

For administration by inhalation the compounds according to the invention are conveniently delivered in the form of an aerosol spray presentation from pressurised packs or a nebuliser, with the use of a suitable propellent, e.g. dichlorodifluoromethane, trichlorofluoromethane, dichlorotetrafluoroethane, carbon dioxide or other suitable gas. In the case of a pressurised aerosol the dosage unit may be determined by providing a valve to deliver a metered amount. Capsules and cartridges of e.g. gelatin for use in an inhaler or insufflator may be formulated containing a powder mix of a compound of the invention and a suitable powder base such as lactose or starch.

For intranasal administration, the compounds according to the invention may be formulated as solutions for administration via a suitable metered or unit dose device or alternatively as a powder mix with a suitable carrier for administration using a suitable delivery device.

The compounds of formula (I) may also be administered in combination with other therapeutic agents. Thus, for example, in the treatment of gastric stasis, symptoms of gastrointestinal dysfunction and nausea and vomiting, the compounds of formula (I) may be administered in combination with antisecretory agents such as histamine $H_2$-receptor antagonists (e.g. ranitidine, sufotidine, cimetidine, famotidine, nizatidine or roxatidine) or $H^+K^+$ATPase inhibitors (e.g. omeprazle). In the treatment of nausea and vomiting, compounds of formula (I) may also be administered in combination with dexamethasone or a cyclo-oxygenase inhibitor such as piroxicam.

A proposed dose of the compounds of the invention for administration to man (of approximately 70 kg body weight) is 0.001 to 100 mg, preferably 0.01 to 50 mg, of the active ingredient per unit does expressed as the weight of free base, which could be administered, for example, 1 to 4 times per day. It will be appreciated that it may be necessary to make routine variations to the dosage, depending on the age and condition of the patient. The dosage will also depend on the route of administration.

Compounds of general formula (I) and physiologically acceptable salts or solvates thereof may be prepared by the general methods outlined hereinafter. In the following description, the groups $R^1$ and Im are as defined for compounds of general formula (I) unless otherwise stated.

According to first general process (A), a compound of general formula (I) may be prepared by reacting a compound of formula (II):

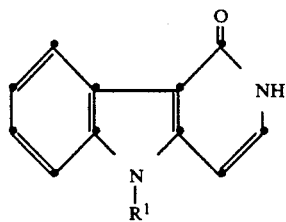
(II)

or a protected derivative thereof, with a compound of formula (III):

(III)

or a protected derivative thereof, wherein L is a leaving atom or group, such as a halogen atom (e.g. chlorine, bromine or iodine), or an acyloxy group (e.g. trifluoroacetyloxy or acetoxy), or a sulphonyloxy group (e.g. trifluoromethanesulphonyloxy, p-toluenesulphonyloxy or methanesulphonyloxy), followed where necessary by removal of any protecting groups. L is preferably a halogen atom (e.g. a chlorine atom).

The reaction may be carried out in an inert solvent such as an ether (e.g. dimethoxyethane, diglyme or tetrahydrofuran), a substituted amide (e.g., dimethylformamide or N-methylpyrrolidone), an aromatic hydrocarbon (e.g. toluene), a ketone (e.g. acetone), or dimethyl sulphoxide, at a temperature between ambient and 100° C., in the presence of a base. Suitable bases include alkali metal hydrides (e.g. sodium hydride), alkali metal carbonates (e.g. sodium carbonate), alkali metal amides (e.g. sodium amide), alkali metal alkoxides (e.g. potassium t-butoxide) or alkali metal hydroxides (e.g. sodium or potassium hydroxide).

According to another general process (B), a compound of general formula (I) may be converted into another compound of formula (I) using conventional techniques. Such conventional techniques include alkylation and acylation using protection and deprotection where necessary.

The term 'alkylation' according to general process (B) includes the introduction of groups such as cycloalkyl, alkenyl or phenyalkyl groups.

Thus, for example, a compound of formula (I) in which $R^1$ represents a $C_{1-6}$alkyl, $C_{3-6}$alkenyl, $C_{3-10}$alkynyl, $C_{3-7}$cycloalkyl, $C_{3-7}$cycloalkyl $C_{1-4}$alkyl, phenyl$C_{1-3}$alkyl, phenylmethoxymethyl, phenoxyethyl or phenoxymethyl group may be prepared by alkylating a compound of formula (I) in which $R^1$ represents a hydrogen atom, or a compound in which $R^3$ represents a $C_{1-6}$alkyl, $C_{3-7}$cycloalkyl, $C_{3-6}$alkenyl or phenyl$C_{1-3}$alkyl group may be prepared by alkylating the corresponding compound of formula (I) in which $R^3$ represents a hydrogen atom, using conventional procedures, for example as described in published European Patent Specification No. 242973. Thus the reactions may be effected using an appropriate alkylating agent of formula $R^7Z$ (where $R^7$ is the group to be introduced and Z is a leaving atom or group), preferably in the presence of a base.

According to another embodiment of general process (B), a compound of formula (I) wherein $R^1$ represents $-CO_2R^5$, $-COR^5$, $-CONR^5R^6$ or $-SO_2R^5$ may be prepared by acylating or sulphonylating as appropriate, a compound of formula (I) wherein $R^1$ represents a hydrogen atom. The acylation/sulphonylation reactions may be effected using an appropriate acylating-/sulphonylating agent according to conventional procedures, for example, as described in published European Patent Specification No. 210840.

It should be appreciated that in the above transformation it may be necessary or desirable to protect any sensitive groups in the molecule of the compound in question to avoid undesirable side reactions. For example, it may be necessary to protect the indole and/or imidazole nitrogen atoms, for example with an arylmethyl (e.g. trityl), alkyl (e.g. t-butyl), alkoxymethyl (e.g. methoxymethyl), acyl (e.g. benzyloxycarbonyl) or a sulphonyl (e.g. N,N-dimethylaminosulphonyl or p-toluenesulphonyl) group.

Thus according to another general process (C), a compound of general formula (I) may be prepared by the removal of any protecting groups from a protected form of a compound of formula (I). Deprotection may be effected using conventional techniques such as those described in 'Protective Groups in Organic Synthesis' by T. W. Greene (John Wiley and Sons, 1981).

For example, a trityl group may be cleaved by acid treatment (e.g. using dilute hydrochloric or acetic acid). An alkoxyalkyl group may be removed using a mineral acid (e.g. dilute hydrochloric acid). An acyl group may be removed by hydrolysis under acidic or basic conditions (e.g. using hydrogen bromide or sodium hydroxide). A sulphonyl group may be removed by alkaline hydrolysis.

Compounds of formula (II) may be prepared, for example, by the method described in published European Patent Specificaton No. 306323A.

Compounds of formula (III) and protected derivatives thereof may be prepared, for example, by methods analogous to that described in published European Patent Specification No. 242973A.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), a halogenated hydrocarbon (e.g. dichloromethane), an ester (e.g. ethyl acetate) or an ether (e.g. tetrahydrofuran).

Physiologically acceptable salts may also be prepared from other salts, including other physiologically acceptable salts, of the compound of formula (I) using conventional methods.

Individual enantiomers of the compound of the invention may be obtained by resolution of a mixture of enantiomers (e.g. a racemic mixture) using conventional means, such as an optically active resolving acid; see for example 'Stereochemistry of Carbon Compounds' by E. L. Eliel (Mc Graw Hill, 1962) and 'Tables of Resolving Agents' by S. H. Wilen.

The methods described above for preparing the compounds of the invention may be used for the introduction of the desired groups at any stage in the stepwise formation of the required compounds, and it will be appreciated that these methods can be combined in different ways in such multi-stage processes. The sequence of the reactions in multi-stage processes should of course be chosen so that the reaction conditions used do not affect groups in the molecule which are desired in the final product.

The invention is further illustrated by the following Example. All temperatures are in °C.

Flash column chromatography (FCC) was carried out on silica (Merck 9385). Solvent System A as used for chromatography denotes dichloromethane:ethanol:0.88 ammonia solution. Organic extracts were dried, where indicated, over magnesium sulphate.

EXAMPLE 2,5-Dihydro-5-methyl-2-[(5-methyl-1H-imidazol-4-yl)methyl]-1H-pyrido[4,3-b]indol-1-one maleate Sodium hydride (73% dispersion in oil; 80 mg) was added to a stirred suspension of 2,5-dihydro-5-methyl-1',uns/H/ -pyrido[4,3-b]indol-1-one (440 mg) in dry dimethoxyethane (25 ml) under nitrogen and the mixture was heated it 50° for 6 h. 4-(Chloromethyl)-5-methyl-1-(triphenylmethyl)-1H-imidazole (910 mg) was then added, and stirring was continued at 50° for 20 h. Water (4.5 ml) and acetic acid (4.5 ml) were added and the solution was heated at reflux for 5 h. The mixture was poured into 8% sodium bicarbonate solution (80 ml) end extracted with dichloromethane:ethanol (10:1; 3×40 ml). The combined, dried organic extracts were evaporated to give a solid (ca. 1.6 g) which was purified by FCC eluting with System A (200:10:1) to give the free base of the title compound as a solid (384 mg). A sample of this solid (100 mg) was dissolved in absolute ethanol (20 ml) and treated with a solution of maleic acid (40 mg) in absolute ethanol (1 ml). The solvent was removed in vacuo and the residue was triturated with dry ether (3×20 ml) to give a solid (115 mg) which was re-crystallised from methanol-ethyl acetate to give the title compound (40 mg), m.p. 166°–168°.

Water Analysis Found 0.49% w/w≡0.11 mol $H_2O$.

Analysis. Found: C,61.1; H,4.9; N,13.3; $C_{17}H_{16}N_4 \cdot 0.11H_2O$ requires C,61.5; H,5.0; N,13.7%.

The following examples illustrate pharmaceutical formulations according to the invention. The term "active ingredient" is used herein to represent a compound of formula (I).

TABLETS FOR ORAL ADMINISTRATION

Tablets may be prepared by the normal methods such as direct compression or wet granulation.

The tablets may be film coated with suitable film forming materials, such as hydroxypropyl methylcellulose, using standard techniques, Alternatively the tablets may be sugar coated.

Tablets of other strengths may be prepared by altering the ratio of active ingredient to excipients or the compression weight and using punches to suit.

| Direct Compression Tablet | |
| --- | --- |
| | mg/tablet |
| Active Ingredient | 0.50 |
| Calcium Hydrogen Phosphate BP* | 87.25 |
| Croscarmellose Sodium NF | 1.80 |
| Magnesium Stearate BP | 0.45 |
| Compression weight | 90.00 |

*of a grade suitable for direct compression.

The active ingredient is passed through a 60 mesh sieve, blended with the calcium hydrogen phosphate, croscarmellose sodium and magnesium stearate. The resultant mix is compressed into tablets using a Manesty F3 machine fitted with 5.5 mm, flat bevelled edge punches.

| INJECTION FOR INTRAVENOUS ADMINISTRATION | | |
| --- | --- | --- |
| | mg/ml | |
| Active ingredient | 0.05 | 1.0 |
| Sodium Chloride BP | as required | as required |
| Water for Injection BP to | 1.0 ml | 1.0 ml |

Sodium chloride may be added to adjust the tonicity of the solution and the pH may be adjusted, using acid or alkali, to that of optimum stability and/or facilitate solution of the active ingredient. Alternatively, suitable buffer salts may be used.

The solution is prepared, clarified and filled into appropriate size ampoules sealed by fusion of the glass. The injection is sterilised by heating in an autoclave using one of the acceptable cycles. Alternatively, the

We claim:

1. A compound of formula (I)

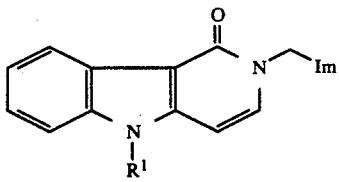

wherein

Im represents an imidazolyl group of the formula:

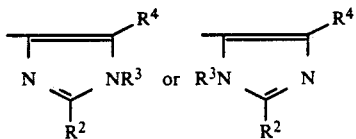

and $R^1$ represents a hydrogen atom or a group selected from $C_{1-6}$alkyl, $C_{3-6}$alkenyl, $C_{3-10}$alkynyl, $C_{3-7}$cycloalkyl, $C_{3-7}$cycloalkyl$C_{1-4}$alkyl, phenyl, phenyl$C_{1-3}$alkyl, phenylmethoxymethyl, phenoxyethyl, phenoxymethyl, $-CO_2R^5$, $-COR^5$, $-CONR^5R^6$ or $-SO_2R^5$ (wherein $R^5$ and $R^6$, which may be the same or different, each represents a hydrogen atom, a $C_{1-6}$alkyl or $C_{3-7}$cycloalkyl group, or a phenyl or phenyl$C_{1-4}$alkyl group, in which the phenyl group is unsubstituted or substituted by one or more $C_{1-4}$ alkyl, $C_{1-4}$alkoxy or hydroxy groups or halogen atoms, with the proviso that $R^5$ does not represent a hydrogen atom when $R^1$ represents a group $-CO_2R^5$ or $-SO_2R^5$);

one of the groups represented by $R^2$, $R^3$ and $R^4$ is a hydrogen atom or a $C_{1-6}$alkyl, $C_{3-7}$cycloalkyl, $C_{3-6}$alkenyl, phenyl or phenyl$C_{1-3}$alkyl group, and each of the other two groups, which may be the same or different, represents a hydrogen atom or a $C_{1-6}$alkyl group;

or a physiologically acceptable salt or solvate thereof.

2. A compound according to claim 1 in which $R^1$ represents a hydrogen atom or a $C_{1-3}$alkyl group.

3. A compound according to claim 1 in which $R^2$, $R^3$ and $R^4$ each independently represent a hydrogen atom or a $C_{1-4}$alkyl group.

4. A compound according to claim 1 in which $R^2$ and $R^3$ each represent a hydrogen atom and $R^4$ represents a $C_{1-3}$alkyl group.

5. 2,5-Dihydro-5-methyl-2-[(5-methyl-1H-imidazol-4-yl)methyl]-1H-pyrido[4,3-b]indol-1-one of a physiologically acceptable salt or solvate thereof.

6. A pharmaceutical composition which comprises an effective amount of a compound of formula (I) as defined in claim 1 or a physiologically acceptable salt or solvate thereof together with at least one physiologically acceptable carrier or excipient.

7. A method of treating a condition mediated through 5-HT$_3$ receptors which comprises administering to a patient an effective amount to relieve said condition of a compound of formula (I) as defined in claim 1 or a physiologically acceptable salt or solvate thereof.

* * * * *